(12) United States Patent
Marcolongo et al.

(10) Patent No.: US 7,214,245 B1
(45) Date of Patent: May 8, 2007

(54) ASSOCIATING HYDROGELS FOR NUCLEUS PULPOSUS REPLACEMENT IN INTERVERTEBRAL DISCS

(75) Inventors: Michele Marcolongo, Landsdowne, PA (US); Anthony Lowman, Wallingford, PA (US)

(73) Assignee: Drexel University, Philadelphia, PA (US)

( * ) Notice: Subject to any disclaimer, the term of this patent is extended or adjusted under 35 U.S.C. 154(b) by 106 days.

(21) Appl. No.: 10/111,782

(22) PCT Filed: Oct. 27, 2000

(86) PCT No.: PCT/US00/29874

§ 371 (c)(1),
(2), (4) Date: Dec. 23, 2002

(87) PCT Pub. No.: WO01/32100

PCT Pub. Date: May 10, 2001

Related U.S. Application Data

(60) Provisional application No. 60/162,338, filed on Oct. 29, 1999.

(51) Int. Cl.
*A61F 2/44* (2006.01)

(52) U.S. Cl. ............................ 623/17.16; 623/17.11; 623/926

(58) Field of Classification Search ........... 623/17.11, 623/17.16, 926
See application file for complete search history.

(56) References Cited

U.S. PATENT DOCUMENTS

| | | | | |
|---|---|---|---|---|
| 5,106,876 | A | * | 4/1992 | Kawamura ................ 522/5 |
| 5,143,071 | A | * | 9/1992 | Keusch et al. ............ 600/397 |
| 5,192,326 | A | | 3/1993 | Bao et al. ................. 623/17 |
| 5,262,475 | A | | 11/1993 | Creasy .................... 525/58 |
| 5,314,478 | A | | 5/1994 | Oka et al. ................ 623/18 |
| 5,458,643 | A | | 10/1995 | Oka et al. ................ 623/18 |
| 5,534,028 | A | * | 7/1996 | Bao et al. ............... 623/17.16 |
| 5,824,093 | A | | 10/1998 | Ray et al. ................ 623/17 |
| 5,846,214 | A | | 12/1998 | Makuuchi et al. .......... 602/52 |
| 5,976,186 | A | * | 11/1999 | Bao et al. ............... 623/17.16 |
| 6,231,605 | B1 | * | 5/2001 | Ku ........................ 623/11.11 |
| 2002/0198599 | A1 | * | 12/2002 | Haldimann ............. 623/17.16 |

FOREIGN PATENT DOCUMENTS

JP          09262279 A  * 10/1997

* cited by examiner

*Primary Examiner*—Paul B. Prebilic
(74) *Attorney, Agent, or Firm*—Stroock & Stroock & Lavan LLP

(57) ABSTRACT

A prosthetic nucleus prepared from blends of polyvinylalcohol and polyvinyl pyrollidone or its copolymers for replacement of the nucleus pulposus in intervertebral discs is provided. Also provided are methods of replacing the nucleus pulposus and treating disc degeneration-associated pain in mammals using this prosthetic nucleus.

6 Claims, No Drawings

ASSOCIATING HYDROGELS FOR NUCLEUS PULPOSUS REPLACEMENT IN INTERVERTEBRAL DISCS

CROSS-REFERENCE TO RELATED APPLICATIONS

This application claims the benefit under 35 U.S.C. 119(e) of U.S. Provisional Patent Application No. 60/162,338, filed Oct. 29, 1999.

BACKGROUND OF THE INVENTION

Over five million Americans suffer from chronic lower back pain, which has become the number one cause of lost work days in the United States. As a result, over 20 billion dollars are spent each year for the treatment of lower back pain, making it one of the most expensive health care issues today.

While the causes of lower back pain remain unclear, it is believed that 75% of cases are associated with degenerative disc disease, where the intervertebral disc of the spine suffers reduced mechanical functionality due to dehydration of the central disc region known as the nucleus pulposus. The reduction in the ability of the disc to transmit loads evenly and efficiently between vertebral bodies leads to damage in the annular region of the disc, known as the annulus fibrosis. Fissures or tears in the annulus can translate into a disc that herniates or ruptures, resulting in impingement of the nerves in the region of the disc. This impingement can lead to lower back or leg pain, depending on which nerves have been affected. Current treatments range from conservative bed rest to highly invasive surgical interventions (e.g., spinal fusion and discectomy) that are aimed at reducing pain but not at restoring disc function.

Spinal fusion is achieved by removal of the entire intervertebral disc, filling the gap or space with a bone graft and providing enough stability to the region through metal fixation plates and screws so that the vertebral bodies will fuse together. Although fusion serves to alleviate pain, the fusion does not restore the physiological biomechanics of the vertebral segment. In fact, the lack of motion within the segment can lead to further degeneration of the more distal intervertebral discs (Leong, J. C. et al. *Spine* 1983 793–799).

Discectomy is employed when the disc has herniated and is impinging on nerve bundles causing pain. In this surgery, the impinging region on the annulus fibrosis is excised, alleviating pressure on the nerves and eliminating pain. Like spinal fusion, however, this approach fails to restore physiological biomechanics of the vertebral segment. Further, the path of disc degeneration is likely to continue and spinal fusion in the future will likely be required.

An alternative approach to treatment of degenerative disease is to remove the diseased disc and replace it with a synthetic implant. Disc replacement may serve to eliminate pain while restoring physiological motion. Designs include low friction sliding surfaces, like a ball and socket (U.S. Pat. No. 5,258,031), spring and hinge systems (U.S. Pat. No. 4,309,777; U.S. Pat. No. 5,320,644; U.S. Pat. No. 4,759,769), contained fluid chambers (U.S. Pat. No. 4,083,477; German Patent DE-OS 3,741,493), and discs of rubber and other elastomers (Edeland, H. G. *J. Biomed. Mater. Res. Appl. Biomater.* 1989 23: 189–194; U.S. Pat. No. 4,911,716; U.S. Pat. No. 5,171,281). None of these concepts has proven effective in returning functionality to the spine segment. Spring and hinge systems cannot adapt to the changing center of rotation of the disc and fluid filled and elastic materials cannot survive the compressive and torsional loading of the spine biomechanics.

Limited clinical treatment with disc replacement has been performed. Human patients have been implanted with a hexene-based carbon black-filled polyolefin rubber core vulcanized to two porous-coated titanium plates (U.S. Pat. No. 5,071,437), with fracture of the rubber core experienced in 2 of 6 patients (Enker, P. et al. *Spine* 1993 18: 1067–1070). Clinical data is also available for the LINK disc replacement which consists of cobalt chromium alloy end plates and a polyethylene core (U.S. Pat. No. 4,759,766). In a 93 patient clinical trial, back pain relief was reported in only 20% of patients and leg pain relief in only 40–50% of patients after an average implantation time of one year (Griffith, S. L. et al. *Spine* 1994 19: 1842–1849).

Attempts have also been made to replace only the nucleus pulposus. Replacement of the nucleus pulposus is expected to arrest the initial dehydration of the degenerated nucleus and return the disc to a fully hydrated state so that the degenerative process, including the associated pain, is postponed or prevented and the mechanical function is restored to the vertebral segment.

Nucleus replacement was first attempted in the early 1960's with self-curing silicone which was injected into the disc space of cadavers (Nachemson, A. *Bull. Hosp. Joint Dis.* 1962 23: 130–132). Silicone showed early promise as a material for nucleus pulposus replacement until silicone synovitis and its associated complications led to limitation of the clinical use of the material (Cham, M. et al. *Skeletal Radiol.* 1998 27: 13–17).

Hydrogels are three-dimensional, water-swollen structures composed of mainly hydrophilic homopolymers or copolymers (Lowman, A. M. and Peppas, N. A., *Hydrogels*, in Encyclopedia of Controlled Drug Delivery, E. Mathiowitz, Ed., John Wiley and Sons, 1999. pp. 397–418)). These materials are for the most part insoluble due to the presence of chemical or physical crosslinks. The physical crosslinks can be entanglements, crystallites or weak associations such as van der Waals forces or hydrogen bonds. The crosslinks provide the network structure and physical integrity. For this reason, hydrogels have also been suggested as a useful material for nucleus replacement. In addition, they can be prepared with mechanical properties similar to the nucleus itself as well as with similar physiological properties, where it maintains about 70% water content under physiological loading conditions. U.S. Pat. No. 5,047,055 and U.S. Pat. No. 5,192,326 describe a hydrogel for use in nucleus pulposus replacement which is comprised of 100% semicrystalline polyvinyl alcohol (PVA) PVA is a biocompatible polymer that has the ability to absorb water or physiological fluid and survive mechanical loading as would exist in the nucleus region of the intervertebral disc.

However, PVA is not entirely stable within the physiological environment of the body. PVA has been found to degrade through the melting out of smaller crystallites over time, thereby resulting in a reduction of mechanical properties and leaching of molecules into the physiological environment. Accordingly, these devices are limited by instability of PVA that results in mass loss and degradation of mechanical properties over time of immersion in vitro or implantation in vivo.

U.S. Pat. No. 5,976,186 discloses a prosthetic nucleus prepared from hydrogels of lightly crosslinked biocompatible homopolymers and copolymers of hydrophilic monomers, HYPAN or highly hydrolyzed crystalline PVA which exhibit an equilibrium water content (EWC) of from about 30 to about 90%. It is taught that partially hydrated xerogel rods or tubes of these hydrogels can be implanted into the nuclear cavity of an intervertebral disc wherein they can be brought to their EWC more rapidly due to their greater surface area.

The present invention relates to a modified PVA hydrogel for use in intervertebral disc replacement, and more specifically replacement of the nucleus pulposus, which has been stabilized by addition of a second polymer, preferably polyvinyl pyrollidone (PVP) or copolymers of PVP and poly(methyl methacrylate), poly(acrylamide), poly(acrylic acid), poly(acrylonitrile) or poly(ethylene glycol). Implantation of this new hydrogel is expected to be particularly effective in mammals, in particular humans, with early diagnosis of disc disease before the annulus has suffered significant degeneration.

SUMMARY OF THE INVENTION

An object of the present invention is to provide a prosthetic nucleus for intervertebral disc replacement which comprises a hydrogel prepared from blends of polyvinyl alcohol and a second polymer such as polyvinyl pyrollidone or its copolymers.

Another object of the present invention is to provide a method for replacement of the nucleus pulposus which comprises implanting into the nuclear cavity of an intervertebral disc a prosthetic nucleus comprising a hydrogel prepared from blends of polyvinyl alcohol and a second polymer such as polyvinyl pyrollidone or its copolymers.

Another object of the present invention is to provide a method of treating intervertebral disc degeneration-associated pain which comprises implanting into an animal suffering from intervertebral disc degeneration-associated pain a prosthetic nucleus comprising a hydrogel prepared from blends of polyvinyl alcohol and a second polymer such as polyvinyl pyrollidone or its copolymers so that intervertebral disc degeneration-associated pain is reduced.

DETAILED DESCRIPTION OF THE INVENTION

It has now been found that addition of polyvinyl pyrollidone (PVP) to polyvinyl alcohol (PVA) produces a hydrogel that is more stable than PVA alone and which maintains adequate mechanical properties as well as biocompatibility to serve as a useful prosthetic nucleus. These gels have unique properties in that no crosslinking agents are required for gelation. Rather, these materials are formed by blending of the polymers and the physical crosslinking occurs due to interchain hydrogen bonding between PVP and PVA as well as intrachain hydrogen bonding due to PVA crystallization. This gelation technique provides for a clean preparation technique without concerns for leaching of unreacted, toxic monomers or crosslinking agents.

Accordingly, the present invention relates to prosthetic nucleus for intervertebral disc replacement which comprise this hydrogel as well as methods for replacement of the nucleus pulposus via implantation of this hydrogel copolymer. Hydrogels for use in the present invention comprise a blend of PVA and 0.1% to 50%, more preferably 1 to 5%, of a second polymer, preferably PVP or copolymers of PVP and poly(methyl methacrylate), poly(acrylamide), poly(acrylic acid), poly(acrylonitrile) or poly(ethylene glycol). In a preferred embodiment, the hydrogel comprises a blend of PVA and 2.5% PVP. It is believed that implantation of the prosthetic nucleus of the present invention will be useful in alleviating the pain in mammals, in particular humans, suffering from intervertebral disc degeneration.

The associating gel composed of PVA and PVP is a "memory" material, meaning that it can remember or regain a given geometry from its hydrated to dehydrated states. This material property can be exploited by inserting the copolymer material as an implant in a dehydrated state into the nuclear cavity of the disc using arthroscopic methods known to those of skill in the art. This allows for insertion of the smaller dehydrated copolymer using a clinical procedure that is minimally invasive. The copolymer can be rehydrated after the insertion using physiological saline. Combination of a minimally invasive procedure with pain relief and potential restoration of functional joint biomechanics serves to make this new copolymer material an important advance for the surgeon and the patient.

Four PVA/PVP copolymer compositions (C2–C5) and pure PVA (C1) hydrogels were synthesized using freeze-thawing techniques (compositions as listed below in Table 1).

TABLE 1

Polymer Compositions Examined for Stability

| Polymer | C1 | C2 | C3 | C4 | C5 |
|---|---|---|---|---|---|
| PVA | 100 | 99.5 | 99.0 | 95.0 | 90.0 |
| PVP | 0 | 0.5 | 1.0 | 5.0 | 10.0 |

A 39 day degradation study was performed to establish the differences between the copolymers and pure PVA. Five samples of each material were immersed in phosphate buffered saline (PBS) solutions at 7.4 pH at 37° C. for 39 days. Before immersion, dry weights of the unswollen polymers were measured and recorded for each sample. For the first 7 days, daily weight measurements were made on each sample, while further measurements were made weekly thereafter.

In the initial part of the study, the PVA gels degraded the least. However, after 3 weeks, C2 and C3 PVA/PVP copolymers showed less weight change than the other samples, including pure PVA (C1). These results indicate that the C2 copolymer, with 0.5% PVP added to PVA, was the most stable hydrogel system. However, both C2 and C3 had improved stability over pure PVA hydrogels.

Additional experiments were performed with copolymers comprising 0, 0.5, 1, 5, 10, 17.5 or 25% PVP (molecular weight=10 kilodaltons) and PVA (molecular weight=143 kilodaltons). Results from these experiments confirmed that addition of PVP to PVA reduced mass loss over 120 days in vitro. Specifically, with 5% PVP added to PVA, there was a 50% increased retention of mass as compared to PVA alone.

The mechanical properties of PVA alone versus a hydrogel comprising 5% PVP and PVA were compared following 2 and 56 days of immersion in vitro. A 15% reduction in modulus of the PVA material was observed during this period of emersion. In contrast, the 5% PVP/PVA hydrogel exhibited a 20% increase in modulus in the same period. This increase in modulus is believed to be due to the increased crystallinity in the polymer blend over time of emersion in vitro. Specifically, the 5% PVP/PVA hydrogel had a change in heat enthalpy from 75.9 to 81.3 over just three weeks immersion in vitro, indicative of increased crystallinity and hydrogen bonding within the polymer.

Using FTIR analysis it was found that the PVA/PVP hydrogels are held together by interchain and intrachain hydrogen bonding. These hydrogen bonds, known as interpolymer complexes, serve as secondary, physical crosslinks, providing networks with additional stability in the event that PVA crystallites melt out of the gel in vivo, as has been shown to occur. Over time of immersion, it was found that the PVP chains are the first to elude, resulting in a reduced mass fraction of PVP with immersion up to 24 hours. Despite this eluding, the PVP still enables stabilization of the crystalline regions within the PVA portion of the polymers, greatly reducing the crystal melting that is seen with PVA alone. This overall decrease in elution of polymer in the body decreases the chances of an inflammatory response due to large polymer dumping in the local region of the nucleus. In addition, the mechanical properties of the copolymer are more stable.

Accordingly, the associating hydrogels of the present invention prepared from a blend of PVA and a second polymer, preferably polyvinyl pyrollidone (PVP) or copolymers of PVP and poly(methyl methacrylate), poly(acrylamide), poly(acrylic acid), poly(acrylonitrile) or poly(ethylene glycol) can be used as a prosthetic nucleus for replacement of nucleus pulposus in mammals, including humans, diagnosed with early degenerative disc disease, without annulus herniation or rupture. One of skill in the art can insert the hydrogels of the present invention in a dehydrated state into the nuclear cavity of an intervertebral disc using standard, marginally invasive surgical techniques or arthroscopic procedures well known in the art. The hydrogels are then rehydrated in situ using, for example, physiological saline. Implantation of the prosthetic nucleus is expected to provide relief from pain as well as provide for functional disc activity.

What is claimed is:

1. A prosthetic nucleus for replacing at least a portion of a natural nucleus pulposus of an intervertebral disc, comprising an associating hydrogel, in said prosthetic nucleus, prepared from a blend polyvinyl alcohol and polyvinyl pyrollidone, wherein the associating hydrogel comprises from 0.5% to 2.5% polyvinyl pyrollidone.

2. A method for replacement of at least a portion of a nucleus pulposus of an intervertebral disc, comprising implanting a prosthetic nucleus comprising an associating hydrogel prepared from a blend of polyvinyl alcohol and polyvinyl pyrollidone into the nuclear cavity of the intervertebral disc, wherein the associating hydrogel comprises from 1% to 5% polyvinyl pyrollidone.

3. A method of treating intervertebral disc degeneration-associated pain in a mammal, comprising implanting a prosthetic nucleus comprising an associating hydrogel prepared from a blend of polyvinyl alcohol and polyvinyl pyrollidone into the nuclear cavity of an intervertebral disc of the mammal so that disc degeneration-associated pain is alleviated, wherein the associating hydrogel comprises from 1% to 5% polyvinyl pyrollidone.

4. A method for replacement of at least a portion of a nucleus pulposus of an intervertebral disc, comprising implanting the prosthetic nucleus of claim 2 into the nuclear cavity of the intervertebral disc.

5. A method of treating intervertebral disc degeneration-associated pain in a mammal, comprising implanting the prosthetic nucleus of claim 2 into the nuclear cavity of an intervertebral disc of the mammal so that disc degeneration-associated pain is alleviated.

6. The prosthetic nucleus of claim 1, wherein the associating hydrogel comprises about 1% polyvinyl pyrollidone.

* * * * *

UNITED STATES PATENT AND TRADEMARK OFFICE
CERTIFICATE OF CORRECTION

PATENT NO. : 7,214,245 B1 Page 1 of 1
APPLICATION NO. : 10/111782
DATED : May 8, 2007
INVENTOR(S) : Michele Marcolongo et al.

It is certified that error appears in the above-identified patent and that said Letters Patent is hereby corrected as shown below:

Column 6, line 23 "nucleus of claim 2" should read --nucleus of claim 1--

Column 6, line 28 "nucleus of claim 2" should read --nucleus of claim 1--

Signed and Sealed this

Twenty-first Day of October, 2008

JON W. DUDAS
*Director of the United States Patent and Trademark Office*